United States Patent [19]
Ribier et al.

[11] Patent Number: 5,650,166
[45] Date of Patent: *Jul. 22, 1997

[54] MOISTURIZING COMPOSITION FOR THE SIMULTANEOUS TREATMENT OF THE SURFACE LAYERS AND DEEP LAYERS OF THE SKIN, AND USE THEREOF

[75] Inventors: Alain Ribier; Jean-Thierry Simonnet, both of Paris; Jean-François Nadaud, Clamart; Isabelle Le Royer, Jouy en Josas, all of France

[73] Assignee: L'Oreal, Paris, France

[*] Notice: The term of this patent shall not extend beyond the expiration date of Pat. No. 5,601,833.

[21] Appl. No.: 366,722

[22] Filed: Dec. 30, 1994

[30] Foreign Application Priority Data

Dec. 30, 1993 [FR] France .................. 93 15864

[51] Int. Cl.⁶ .................. A61K 9/127; A61K 7/00
[52] U.S. Cl. .................. 424/450; 424/401; 514/844; 514/847
[58] Field of Search .................. 424/450; 514/401, 514/844, 847

[56] References Cited

U.S. PATENT DOCUMENTS 5,422,120  6/1995  Kim .................. 424/450

FOREIGN PATENT DOCUMENTS

| | | |
|---|---|---|
| 0433131 | 6/1991 | European Pat. Off. . |
| 0559502 | 9/1993 | European Pat. Off. . |
| 2315991 | 1/1977 | France . |
| 2408387 | 6/1979 | France . |
| 2614787 | 11/1988 | France . |

OTHER PUBLICATIONS

International Journal of Pharmaceutics, vol. 62, No. 1, Jul. 15, 1990, NL pp. 75–79, Gabrijelcic et al. "Liposomes as drug cariers into the skin by one-dimensional epr imaging".

*Primary Examiner*—Gollamudi S. Kishore
*Attorney, Agent, or Firm*—Oblon, Spivak, McClelland, Maier & Neustadt, P.C.

[57] ABSTRACT

Moisturizing composition for the simultaneous treatment of the surface layers and deep layers of the skin, and use thereof. The composition of the invention comprises a first dispersion of lipid vesicles which are capable of penetrating into the deep layers of the skin and which contain at least one active agent selected from the group consisting of polyols, sugars, proteins, vitamins and the derivatives thereof, ceramides, essential fatty acids, and sterols, for treating these deep layers, and a second dispersion of lipid vesicles which are capable of penetrating into the surface layers of the skin and which contain at least one active agent selected from the group consisting of polyols, nitrogen-containing carboxylic acid derivatives, keratolytic agents, inorganic salts and lipoamino acids, for treating these surface layers.

15 Claims, No Drawings

MOISTURIZING COMPOSITION FOR THE SIMULTANEOUS TREATMENT OF THE SURFACE LAYERS AND DEEP LAYERS OF THE SKIN, AND USE THEREOF

BACKGROUND OF THE INVENTION

1. Field of the Invention

The invention relates to a cosmetic and/or dermatological composition intended to moisturize the skin, both of the face and of the body, or even of the scalp, and the nails. It relates more particularly to a moisturizing composition of this type comprising at least one active agent which is conveyed via at least two distinct types of lipid vesicles.

The invention also relates to a cosmetic use of this composition for moisturizing the skin, and to a process for moisturizing the skin.

2. Discussion of the Background

Many examples are known of cosmetic or dermatological compositions intended for treating the skin, which have one or more active agents that are suitable for treating the skin and which are encapsulated in lipid spherules or vesicles (also known as liposomes).

Lipid spherules or vesicles are understood to refer to particles formed of a membrane consisting of one or more concentric lamellae, these lamellae containing one or more bimolecular layers of amphiphilic lipids encapsulating an aqueous phase. The aqueous phase may contain water-soluble active substances and the bimolecular layers of amphiphilic lipids may contain lipophilic active substances. These spherules generally have a mean diameter of between 10 nm and 5,000 nm.

Among the many documents published regarding this matter, there may be mentioned the French Certificate of Addition 2,408,387 which describes a composition based on aqueous dispersions of ionic or nonionic lipid spherules encapsulating at least one active substance. More precisely, this document describes compositions containing at least two dispersions of spherules containing different active agents, for the purpose of obtaining a mixed system, that is to say a system in which a first dispersion of spherules containing a first category of active substance is combined with a second dispersion of spherules containing another category of active substance, which enables the two types of substances to act simultaneously at the time of treatment and possibly to obtain a synergistic effect which would not be produced if these two types of substances were made to act successively and separately.

Now, it is fully appreciated that it is important for the skin to be well moisturized, both at the surface and in the deeper layers of the epidermis and of the dermis. Exposure of the skin to the atmosphere results in dehydration, which must be compensated for by provision of moisturizing active agents.

It is well known that the skin consists of surface layers, the stratum corneum, and of deep layers, the live epidermis and the dermis. Now, specific delivery of such an active agent into the surface layers and, simultaneously, of the same or another active agent into the deep layers, was not known from the prior art.

Thus, there remains a need for a method and composition for simultaneously moisturizing the surface and deep layers of skin.

SUMMARY OF THE INVENTION

Accordingly one object of the invention is a composition for simultaneously moisturizing the surface layers and deep layers of the skin, comprising:

i) a first dispersion of lipid vesicles which are capable of penetrating into the deep layers of the skin and which contain at least one active agent selected from the group consisting of polyols, sugars, proteins, vitamins and the derivatives thereof, ceramides, essential fatty acids and sterols, for treating these deep layers; and ii) a second dispersion of lipid vesicles which are capable of penetrating into the surface layers of the skin and which contain at least one active agent selected from the group consisting of polyols, nitrogen-containing carboxylic acid derivatives, keratolytic agents, inorganic salts and lipoamino acids, for treating these surface layers.

According to a specific embodiment, the active agents contained in the first dispersion of vesicles and in the second are the same.

The inventors have now developed cosmetic and/or dermatological moisturizing compositions, which allow the simultaneous action of two different active agents, and which furthermore allow these active agents to act in different areas of the skin, that is to say in the surface layers and in the deep layers of the skin, thereby very markedly enhancing the effectiveness of these compositions and the complementary or synergistic effect of the moisturizing active agents used.

The inventors have also developed cosmetic and/or dermatological moisturizing compositions, which enable the same active agent to act simultaneously in the surface layers and in the deep layers of the skin, providing a more complete and therefore a more effective treatment of the skin.

DETAILED DESCRIPTION OF THE PREFERRED EMBODIMENTS

The Applicants have used a means of classifying vesicles which enables a person skilled in the art readily to select lipid vesicles capable of conveying the active agent to the deep layers of the skin, known as vesicles with deep-down action, and those capable of conveying the active agent to the surface layers of the skin, known as vesicles acting at the surface.

This classification is made on the basis of the diffusion constant D of a probe introduced into the vesicles. This probe is ASL (N-(1-oxyl-2,2,6,6-tetramethyl-4-piperidyl)-N,N-dimethyl-N-hydroxyethylammonium iodide], of formula:

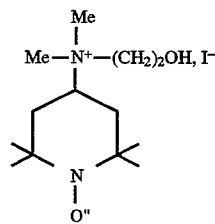

Vesicles for which the diffusion constant D of the probe into the stratum corneum is $>1\times10^{-7}$ $cm^2s^{-1}$ are vesicles which are capable of penetrating into the deep layers of the skin.

Vesicles for which the diffusion constant D of the probe into the stratum corneum is $<1\times10^{-7}$ $cm^2s^{-1}$ are vesicles which are capable of conveying the active agent to the surface layers of the skin.

The vesicles of the first category, the so-called vesicles with deep-down action, are generally in the fluid state at room temperature (about 20° C.), and those of the second category, the so-called vesicles acting at the surface, are generally in the gelled state at room temperature. The means of recognizing the state of the vesicles consists in determining the phase (fluid-gel lamellar) transition temperature of the main lipid constituting the membrane thereof, by differential thermal analysis (DTA).

Other characteristics of these vesicles relate to their ability to deliver the active agent to a greater or lesser depth in the skin. This is particularly the case for the degree of encapsulation.

Glucose is a labelling agent conventionally used for this type of determination (cf. in particular *Liposomes a practical approach* by R. R. C. New, IRL Press (1990), p. 125–136).

The degree of encapsulation is expressed as the volume of glucose solution encapsulated in the vesicles, measured in μl based on the unit weight (mg) of the lipids constituting the membrane. This degree of encapsulation is determined immediately after the step of separation of the free glucose and of the encapsulated glucose ($T_0$), as well as twenty-four hours after this separation ($T_{24}$ hours).

The difference between these two successive determinations illustrates the permeability of the vesicles with respect to the encapsulated glucose, which may also be referred to as their encapsulation potential.

The first category of vesicles (delivering the active agent into the deep layers of the skin) has a high encapsulation potential for the small water-soluble molecules which are conventionally modelled by glucose, this encapsulation potential being maintained for at least 24 hours. The second category of vesicles (delivering the active agent into the surface layers of the skin) does not retain glucose in the encapsulated state for the same amount of time.

The main lipids constituting the vesicles of the first category (deep delivery of the active agent) are composed of at least one linear and saturated fatty chain of length ranging from 16 to 30 carbon atoms, such as hydrogenated phospholipids (from plants or from egg), saturated synthetic phospholipids such as dipalmitoylphosphatidylcholine, and polyol alkyl ethers or polyol alkyl esters containing one, two or three fatty chains per molecule. These lipids are used alone or as a mixture.

The main lipids constituting the vesicles of the second category (active agent delivered at the surface) are chosen in particular from the group comprising ionic lipids, especially such as natural plant- or egg-based phospholipids, containing unsaturated fatty chains having from 16 to 30 carbon atoms; nonionic lipids such as in particular polyol alkyl ethers or polyol alkyl esters containing at least one fatty chain per molecule, including at least one fatty chain with a length of less than 16 carbon atoms, such as lauryl polyglyceryl-6-cetearyl glycol ether; and mixtures thereof. This last compound is described in detail in Patent Application FR 92-09603 filed by L'Oréal.

It is possible, in a known manner, to incorporate into the lipid phase constituting the lipid membrane of the vesicles, at least one additive selected from the group consisting of the group formed of sterols (phytosterols, cholesterol or polyoxyethylenated phytosterols); long-chain alcohols, diols and triols (phytanetriol), long-chain amines and the quaternary ammonium derivatives thereof; phosphoric esters of fatty alcohols and the alkali metal (Na or K) salts thereof, such as dicetyl phosphate, sodium dicetyl phosphate, alkyl sulphates (sodium cetyl sulphate), alkali metal salts of cholesterol sulphate or of cholesterol phosphate, the sodium salt of phosphatidic acid, and lipoamino acids and the salts thereof, such as the sodium acylglutamates.

Examples of vesicles of the first category (delivering the active agent into the deep layers of the skin) which may be mentioned are vesicles obtained from the following lipids (CTFA name):

A/cholesterol/casein lipoamino acid, especially in 45/45/10 weight ratio (where A is a triglyceryl cetyl ether marketed by the company Chimex under the name CHIMEXANE NL);

B/cholesterol/dicetyl phosphate, especially in a 60/35/5 weight ratio (where B is a mixture of triglyceryl mono-, di- and tricetyl ether, marketed by the company Chimex under the name CHIMEXANE NT);

Span 40 (from ICI, or sorbitan palmitate)/cholesterol/sodium acylglutamate (marketed under the name HS11 by the company Ajinomoto), especially in a 47.5/47.5/5 weight ratio;

PEG 8 stearate/cholesterol/sodium acylglutamate, especially with a 47.5/47.5/5 weight ratio (where PEG 8 stearate is polyethylene glycol containing 8 units of ethylene oxide, marketed by Unichema under the name PEG 400 stearate);

PEG 8 stearate/cholesterol/phytanEtriol/sodium acylglutamate, especially with a 47.5/20/27.5/5 weight ratio;

Hydrogenated lecithin/polyoxyethylenated phytosterol containing 5 units of ethylene oxide, especially in a 60/40 weight ratio;

Polyoxyethylenated methylglucose distearate containing 20 units of ethylene oxide/cholesterol/sodium acylglutamate, especially in a 45/45/10 weight ratio (the distearate being, for example, that marketed under the name GLUCAM E 20 distearate by Amerchol);

A/cholesterol/dicetyl phosphate, especially with a 47.5/47.5/5 weight ratio (where A is a triglyceryl cetyl ether marketed by the company Chimex under the name CHIMEXANE NL);

Diglyceryl distearate (for example that marketed by Nihon under the name EMALEX DS G2)/cholesterol/sodium acylglutamate, in a 45/45/10 weight ratio;

Sucrose mono- and distearate (for example GRILLOTEN PSE 141 G from Grillo)/cholesterol/sodium acylglutamate, especially in a 45/45/10 weight ratio;

Tetraglyceryl tristearate (for example TETRAGLYN 3S from Nikkol)/cholesterol/sodium acylglutamate, especially in a 45/45/10 weight ratio.

Examples of vesicles of the second category (delivering the active agent into the surface layers of the skin) which may be mentioned are vesicles obtained from the following lipids:

Sunflower lecithin;

NAPITIDE II (soya lecithin/ethanol/water in a 20/16/64 weight ratio, marketed by Nattermann);

C (soya lecithin/cholesterol/propylene glycol in a 60/20/20 weight ratio, marketed by Nattermann under the name NAT 50 PG);

D/dimyristyl phosphate, especially in a 95/5 weight ratio (where D is a lauryl polyglyceryl-6-cetearyl glycol ether marketed by Chimax under the name CHIMEXANE NS).

Table I below gives, for same of the vesicles obtained using the above lipids, the diffusion constant D for ASL in the stratum corneum and in the epidermis/dermis, as well as the degree of encapsulation of glucose and the phase transition temperature of the main lipid constituting the membrane. The diffusion constant was measured for an encapsulated ASL concentration of 0.35% by weight based on the total weight of the composition.

TABLE I

| Ref. | LIPID SYSTEMS | Proportions % by weight (mg) | Diffusion coefficient $D$ in $10^{-7}$ cm² s⁻¹ in the stratum corneum | Diffusion coefficient $D$ in $10^{-7}$ cm² s⁻¹ in the epidermis/ dermis | Degree of encapsulation of glucose in µl/mg $T_o$ | Degree of encapsulation of glucose in µl/mg $T_{24h}$ | Phase transition temperature in °C. |
|---|---|---|---|---|---|---|---|
| | 1st type - deep down | | | | | | |
| 1 | A/cholesterol/casein lipoamino acid | 45/45/10 (67.5/67.5/15) | 42 | 5 | 7.5 | 6.8 | 50 |
| 2 | B/cholesterol/dicetyl phosphate | 60/35/5 (90/52.5/7.5) | 58 | 2 | 11.1 | 11.1 | 54 |
| 3 | Span 40/cholesterol/ sodium acylglutamate | 47.5/47.5/5 (71.25/71.25/7.5) | 42 | 2 | 13.8 | 13.8 | 50 |
| 4 | PEG 8 stearate/ cholesterol/sodium acylglutamate | 47.5/47.5/5 (71.25/71.25/7.5) | 42 | 2 | 14.4 | 14.4 | 55 |
| 5 | PEG 8 stearate/ cholesterol/phytanetriol/ sodium acylglutamate | 47.5/20/27.5/5 (71.25/30/ 41.25/7.5) | 8.3 | 2.5 | 4.1 | 3.0 | 55 |
| 6 | Hydrogenated lecithin/ polyoxyethylenated phytosterol | 60/40 (90/60) | 8 | 2 | 6.0 | 4.8 | 80 |
| | 2nd type - surface | | | | | | |
| 7 | Sunflower lecithin | 100 (150) | 0.3 | 0.2 | 1.6 | 0 | <0 |
| 8 | Natipide II (soya lecithin/ethanol/water) | 20/16/64 (30/24/96) | 0.4 | 0.2 | 0.4 | 0 | <0 |
| 9 | C (soya lecithin/ sterols/propylene glycol) | 60/20/20 (90/30/30) | 0.25 | 0.1 | 1.8 | 0 | <0 |
| 10 | D/dimyristyl phosphate | 95/5 (142.5/7.5) | 0.3 | 0.2 | 2.0 | 0 | 14 |

Measurement of the diffusion constant D is carried out by combining two methods using a paramagnetic probe, ASL: one-dimensional and periodic electron paramagnetic resonance (EPR), on the one hand, and EPR kinetic imaging, on the other hand. These two methods are respectively described in the articles "Evaluation of liposomes as drug carriers into the skin by one-dimensional EPR imaging" by V. Gabrijelcic et al., International Journal of Pharmaceutics, 62 (1990) p. 75–79, Elsevier, and "Liposome entrapped molecules penetration into the skin measured by nitroxide reduction kinetic imaging" by V. Gabrijelcic et al., Periodicum Biologorum vol. 93, No. 2, p. 245–246, (1991).

Measurement of the degree of encapsulation is carried out as described in the RRC New document cited above, and that of the phase transition temperature is carried out as described above.

Advantageously, several active agents are used simultaneously in each category of vesicles, these active agents having the same function and/or imparting to the skin, at the surface and deep down, the same type of effect; the agents active at the surface and the agents with deep-down action are thus complementary.

The active agents which may be used in the invention are those which are conventionally used in the cosmetic or dermatological field.

The active agents with deep-down action are selected from the group consisting of polyols, sugars, proteins, vitamins and the derivatives thereof, ceramides, essential fatty acids and sterols.

As polyols which may be used in the invention, there may be mentioned glycerine, sorbitol, D-panthenol and mannitol.

As sugars which may be used in the invention, there may be mentioned fructose, galactose, sucrose and N-acetylglucosamine.

As proteins which may be used in the invention, there may be mentioned plant proteins (wheat, soya) and the hydrolysates thereof, peptides and polypeptides, hydroxyproline, filagrine and the precursors thereof, collagen and the hydrolysates thereof, elastin and the derivatives thereof, amino acids (alanine, glycine, citrulline and threonine), and glycosaminoglycans and the derivatives thereof (sulphates).

As vitamins which may be used in the invention, there may be mentioned ascorbic acid (vitamin C) and the derivatives thereof (magnesium ascorbyl phosphate).

As essential fatty acids which may be used in the invention, there may be mentioned linoleic acid and linolenic acid.

As sterols which may be used in the invention, there may be mentioned cholesterol and the derivatives thereof (sulphate and phosphates and soya phytosterols.

As ceramides which may be used in the invention, there may be mentioned ceramides and glycoceramides of plant or animal origin, synthetic ceramides, in particular oleyldihydrosphingosine, and pseudoceramides.

The agents active at the surface are selected from the group consisting of polyols, nitrogen-containing carboxylic acid derivatives, keratolytic agents and inorganic salts.

As polyols active at the surface which may be used in the invention, there may be mentioned glycerine, sorbitol, diglycerol and aminopolyols.

As nitrogen-containing carboxylic acid derivatives which may be used in the invention, there may be mentioned urea, pyrrolidonecarboxylic acid and the derivatives thereof (sodium salt), acetamide and the salts thereof (methylamine), and lipoamino acids such as N-hexadecyloxycarbonylserine or N-oleylglycylserine.

As inorganic salts which may be used in the invention, there may be mentioned inorganic chlorides and in particular sodium chloride and magnesium chloride.

As keratolytic agents which may be used in the invention, there may be mentioned α-hydroxy acids and in particular acids such as lactic acid, glycolic acid, malic acid, tartaric acid, citric acid and is mixtures thereof.

The active agents may represent from 0.02% to 10% of the total weight of the composition. In addition, the 2 types of vesicles may contain other cosmetic active agents such as depigmenting agents and plant extracts.

The compositions according to the invention may be provided in all the pharmaceutical forms normally used for topical application, such as aqueous gels, emulsions, lotions, ointments, sera and, more particularly, vesicle-dispersed oil droplets such as those described in French patents FR-A-2, 485,921 and FR-A-2,490,504.

As is known, in addition to the vesicles, a vegetable oil, mineral oil, silicone-containing oil or synthetic oil which is dispersed in an aqueous phase, and also hydrophilic adjuvants such as gelling agents, preserving agents, opacifying agents, lipophilic adjuvants such as essential oils and fragrances, pigments and fillers, may be found in the compositions of the invention, as described in the above French patents. The dispersed oil may represent from 2% to 40% by weight based on the total weight of the composition, and the adjuvants may represent from 0.1% to 10% by weight in total.

The total weight of vesicle contained in the composition is preferably from 1 to 90 wt. %, more preferably from 5 to 70 wt. %, most preferably from 5 to 20 wt.% based on the total weight of the composition.

The ratio of the amount of vesicles of the first dispersion type which are capable of penetrating into the deep layers to the second dispersion type which are capable of penetrating into the surface layers is preferably from 1:9 to 9:1, more preferably from 3:7 to 7:3, most preferably from 4:6 to 6:4.

Within the context of the following examples the term qs 100 g is an amount needed to bring the total amount of the composition to 100 g.

Other characteristics and advantages of the invention will emerge more clearly from the description, given as an illustration and with no limitation being implied, which follows.

A) Production of lipid vesicles containing ASL

The constituent lipids of the wall of the vesicles are weighed out and dissolved in 10 ml of methanol. The alcoholic solution is then transferred into a 50-ml round-bottomed flask with a ground joint, which is subsequently placed on a rotary evaporator such that the contents are thermostatted at a temperature of 30° C. The evaporation is continued until a dry film of lipid is deposited on the wall of the flask.

3 ml of an aqueous 0.01 molar solution of ASL are then added to the flask, which is subsequently shaken by hand for about 10 minutes, either at room temperature (20° C.) for the vesicles of Table I of reference Nos. 7 to 10, or at a temperature of 50° C. for the vesicles of reference Nos. 1 to 6 of Table I. The medium is then left to equilibrate at room temperature for 2 hours, after which the dispersion is placed in a dialysis bag and in contact with 500 ml of distilled water. Dialysis takes place overnight. The next day, the water is changed and the dialysis in continued for a further 4 hours.

A cotton thread 0.3 mm thick is then soaked in the vesicle dispersion and then placed in contact with a section of skin cut from a pig's ear which has been freshly taken from an abattoir intended for food supply.

The ear sample taken is rinsed with water and cut into slices 1 mm thick, 5 mm wide and 10 mm long and then placed in a maintenance cell. Measurements of the diffusion of ASL into the skin are made in the 24 hours following the taking of the skin sample.

B) Production of the cosmetic composition

1 Production of vesicles of first category (diffusing deep down).

The vesicles (with deep-down action) are prepared according to a common method for co-fusion of the various membrane constituents chosen (see Table I). Thus, the membrane constituent having the lowest melting point $T_m$ is melted; the other membrane constituents are added, and the mixture is then homogenized with moderate stirring and is finally partially hydrated, while maintaining the melting temperature $T_m$ defined above.

An aqueous solution of at least one first active agent for the deep-down treatment is added to the paste obtained. The mixture is stirred with a turbine for 1 h, 30 min in order to hydrate fully, while maintaining the temperature $T_m$. One or more other active agents for the deep-down treatment are added to the reaction medium, homogenization is carried out and the temperature of the medium is lowered to room temperature (20° C.).

2 Production of vesicles of the second category (diffusing at the surface)

An aqueous solution of one (or more) second active agents for the surface treatment is introduced, at room temperature (20° C.) and with simple stirring, into the chosen mixture of constituents which are to form the membrane of the vesicles acting at the surface (see Table I). Vesicles acting at the surface encapsulating the second active agent acting at the surface are thus obtained.

3 Production of the "double-liposome" composition

The fatty phase (the oils) of the composition is added to the medium containing the vesicles with deep-down action and it is dispersed (at room temperature) with stirring. The reaction medium obtained is then mixed with that containing the vesicles acting at the surface. The adjuvants, such as preserving agents, a gelling agent which may be neutralized if necessary with a base (triethanolamine or sodium hydroxide), and fragrances, etc., are then optionally added.

The product obtained is in the form of a soft and smooth white cream which may be used in the cosmetic and/or dermatological field for moisturizing the skin at the surface and deep down. This cream may be used daily. A specific example of a cosmetic composition in accordance with the invention is given below.

EXAMPLE

Double-liposome moisturizing cream

Vesicles with deep-down action

| | |
|---|---|
| PEG 8 stearate/cholesterol/sodium acylglutamate in a 47.5/47.5/5 weight ratio | 3.0% |
| Wheat glycoceramide | 0.15% |
| Collagen hydrolysate (active agent) | 0.5% |
| Soya protein hydrolysate (active agent) | 0.5% |

Vesicles acting at the surface

| | |
|---|---|
| NATIPIDE II marketed by Nattermann | 3.0% |
| Glycerine (active agent) | 0.5% |
| Sodium pyrrolidonecarboxylate (active agent) | 0.4% |

Fatty Phase

| | |
|---|---|
| Vegetable oils | 13.0% |
| Karite butter | 4.0% |
| volatile silicone oil | 4.0% |
| Fragrance | 0.4% |

Aqueous Phase:

| | |
|---|---|
| Preserving agent | 0.3% |
| carboxyvinyl polymer (gelling agent) | 0.4% |
| Sodium hydroxide | qs pH 6 |
| Water | qs 100% |

Obviously, numerous modifications and variations of the present invention are possible in light of the above teachings. It is therefore to be understood that within the scope of the appended claims, the invention may be practiced otherwise than as specifically described herein.

This application is based on French Patent Application 93/15864, filed with the French Patent Office on Dec. 30, 1993, the entire contents of which are hereby incorporated by reference.

What is claimed as new and is desired to be secured by Letters Patent of the United States is:

1. A moisturizing composition for simultaneous treatment of the layers of the stratum corneum and deep layers of the skin, comprising a dispersion mixture of:

i) a first dispersion of lipid vesicles which are capable of penetrating into said deep layers of the skin and which contain at least one active agent having moisturizing activity in the deep layers of the skin, for treating said deep layers; and ii) a second dispersion of lipid vesicles which are capable of penetrating into said layers of the stratum corneum of the skin and which contain at least one active agent selected from the group consisting of a keratolytic agent and a moisturizing agent having moisturizing activity in the layers of the stratum corneum, for treating these layers of the stratum corneum, and wherein said vesicles of said first dispersion ensure a distribution of N-(1-oxyl-2,2,6,6-tetramethyl-4-piperidyl)-N-dimethyl-N-hydroxyethylammonium iodide (ASL) in the stratum corneum $>1\times10^{-7}$ $cm^2/s$ and in that said vesicles of said second dispersion ensure a distribution of ASL in the stratum corneum $<1\times10^{-7}$ $cm^2/s$.

2. The composition of claim 1, wherein said vesicles of said first dispersion are in a fluid state at room temperature and said vesicles of said second dispersion are in a gelled state at room temperature.

3. The composition of claim 1, wherein said vesicles of said first dispersion provide an encapsulation potential of glucose for at least 24 hours, and said vesicles of said second dispersion provide an encapsulation potential of glucose for less than 24 hours.

4. The composition of claim 1, wherein said vesicles of said first dispersion are formed of lipids comprising at least one linear and saturated fatty chain having from 16 to 30 carbon atoms.

5. The composition of claim 1, wherein said vesicles of said first dispersion are formed of at least one lipid selected from the group consisting of natural ionic phospholipids, saturated synthetic phospholipids, polyol alkyl ethers containing at least one linear fatty chain, polyol alkyl esters containing at least one fatty chain and a mixture thereof.

6. The composition of claim 1, wherein said vesicles of said first dispersion are formed of lipids selected from the group consisting of:

triglyceryl cetyl ether, cholesterol, and casein lipoamino acid;

a mixture of triglyceryl mono-, di- and tricetyl ether, cholesterol, and dicetyl phosphate;

triglyceryl cetyl ether, cholesterol, and dicetyl phosphate;

sorbitan palmitate, cholesterol, and sodium acylglutamate;

PEG 8 stearate, cholesterol, and sodium acylglutamate;

diglyceryl distearate, cholesterol, and sodium acylglutamate;

sucrose mono- and distearate, cholesterol, and sodium acylglutamate;

PEG 8 stearate, cholesterol, phytanetriol, and sodium acylglutamate;

polyoxyethylenated methylglucose distearate containing 20 mol of ethylene oxide, cholesterol, and sodium acylglutamate;

hydrogenated lecithin, and polyoxyethylenated phytosterol; and tetraglyceryl tristearate, cholesterol, and sodium acylglutamate.

7. The composition of claim 1, wherein said vesicles of said second dispersion are formed of lipids selected from the group consisting of natural ionic phospholipids having unsaturated fatty chains having from 16 to 30 carbon atoms, polyol alkyl ethers having at least one fatty chain per molecule, comprising at least one fatty chain with a length of less than 16 carbon atoms, polyol alkyl esters having at least one fatty chain per molecule, comprising at least one fatty chain with a length of less than 16 carbon atoms.

8. The composition of claim 1 wherein said vesicles of said second dispersion are formed of at least one lipid selected from the group consisting of sunflower lecithin; soya lecithin, ethanol, and water; soya lecithin, cholesterol, and propylene glycol; and lauryl polyglyceryl-6-cetearyl glycol ether and dimyristyl phosphate.

9. The composition of claim 1, wherein said active agent of said first dispersion and said active agent of said second dispersion provide the same function, the same effect or both.

10. The composition of claim 1, wherein said active agent of said first dispersion and said active agent of said second dispersion are the same.

11. The composition of claim 1 wherein said active agent contained in said first dispersion is selected from the group consisting of glycerine, sorbitol, D-panthenol, mannitol, fructose, galactose, sucrose, N-acetylglucosamine, a protein, a hydrolyzate of a protein, a peptide, a polypeptide, an amino acid, a glycosaminoglycan, ascorbic acid, an essential fatty acid, cholesterol, a ceramide, a glycoceramide, a pseudoceramide and a mixture thereof.

12. The composition of claim 1 wherein said active agent contained in said second dispersion is selected from the group consisting of glycerine, sorbitol, diglycerol, an aminopolyol, urea, pyrrolidonecarboxylic acid, acetamide, an acetamide salt, a lipoamino acid, an inorganic chloride, an alpha-hydroxy acid and a mixture thereof.

13. The composition of claim 1, further comprising iii) an oily phase which is dispersed in an aqueous phase.

14. The composition of claim 1, further comprising iv) a hydrophilic adjuvant or a lipophilic adjuvant.

15. A method for moisturizing the skin, comprising applying to the skin of a subject in need thereof, an effective amount of a composition comprising a dispersion mixture of:

i) a first dispersion of lipid vesicles which are capable of penetrating into deep layers of the skin and which contain at least one active agent having moisturizing activity in the deep layers of the skin, for treating said deep layers; and ii) a second dispersion of lipid vesicles which are capable of penetrating into the layers of the stratum corneum of the skin and which contain at least one active agent selected from the group consisting of, a keratolytic agent and a moisturizing agent having moisturizing activity in the layers of the stratum corneum, for treating said layers of the stratum corneum, and wherein said vesicles of said first dispersion ensure a distribution of N-(1-oxyl-2,2,6,6-tetramethyl-4-piperidyl)-N-dimethyl-N-hydroxyethylammonium iodide (ASL) in the stratum corneum $>1\times10^{-7}$ cm$^2$/s and in that said vesicles of said second dispersion ensure a distribution of ASL in the stratum corneum $<1\times10^{-7}$ cm$^2$/s.

* * * * *